(12) United States Patent
Cheng et al.

(10) Patent No.: US 9,112,158 B1
(45) Date of Patent: Aug. 18, 2015

(54) ASYMMETRIC STYRENE DERIVATIVES HAVING CARBAZOLE AND ANILINE AND ORGANIC LIGHT EMITTING DIODE USING THE SAME

(71) Applicant: National Tsing Hua University, Hsinchu (TW)

(72) Inventors: Chien-Hong Cheng, Hsinchu (TW); Yi-Hsiang Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/323,675

(22) Filed: Jul. 3, 2014

(30) Foreign Application Priority Data

Mar. 14, 2014 (TW) .............................. 103109352 A (51) Int. Cl.
- H01L 27/00 (2006.01)
- H01L 51/00 (2006.01)
- H01L 27/32 (2006.01)
- H01L 51/52 (2006.01)
- H01L 51/50 (2006.01)

(52) U.S. Cl.
CPC ........ *H01L 51/0061* (2013.01); *H01L 27/3211* (2013.01); *H01L 51/0072* (2013.01); *H01L 51/5012* (2013.01); *H01L 51/5016* (2013.01); *H01L 51/5206* (2013.01); *H01L 51/5221* (2013.01)

(58) Field of Classification Search
CPC .............. H01L 51/0043; H01L 51/006; H01L 51/0072; H01L 51/5012; H01L 51/5016; H01L 27/3211; H01L 27/322; C09K 2211/1044; C09K 11/06
See application file for complete search history.

(56) References Cited

U.S. PATENT DOCUMENTS

| | | | |
|---|---|---|---|
| 2002/0041979 A1* | 4/2002 | Taguchi ........................ | 428/690 |
| 2013/0126856 A1* | 5/2013 | Yokoyama et al. ............. | 257/40 |

* cited by examiner

*Primary Examiner* — Victor A Mandala
*Assistant Examiner* — Quovaunda V Jefferson
(74) *Attorney, Agent, or Firm* — Muncy, Geissler, Olds & Lowe, P.C.

(57) ABSTRACT

Asymmetric styrene derivatives having carbazole and aniline are provided with main BCzVBi structure but impair the symmetry of BCzVBi so as to increase the solubility and applicability in OLED solution process. An OLED device using the asymmetric styrene derivatives is also herein disclosed.

12 Claims, 2 Drawing Sheets

ASYMMETRIC STYRENE DERIVATIVES HAVING CARBAZOLE AND ANILINE AND ORGANIC LIGHT EMITTING DIODE USING THE SAME

BACKGROUND OF THE INVENTION

1. Field of the Invention

The present invention relates to asymmetric styrene derivatives having carbazole and aniline and organic light emitting diode using the same, and particularly to asymmetric styrene derivatives having carbazole and aniline provided with main BCzVBi structure but impair the symmetry of BCzVBi, and organic light emitting diode using the same.

2. Description of the Prior Art

OLED (organic light emitting diode), also commonly known as an organic electroluminescent device, is kind a light emitting diode (LED) having organic layer as active layer. Since the organic electroluminescent device provides advantages of self-illumination, wider visual angle (>170°), shorter response time (~μs), higher contrast, higher efficiency, lower power consumption, higher brightness, low operate voltage (3-10 V), thinner size (<2 mm), flexibility and the like, it has been gradually used in flat panel display in recent years. In comparison to liquid crystal display, the organic electroluminescent device provides with OLED pixel array having self-luminous characteristics and therefore do not require additional back light module; to apply OLED into a full-color display, it is necessary and important to develop red, green, and blue light emitting materials with appropriate chromaticity and high light-emitting efficiency.

Excitons generated from recombining holes and electrons may have triplet state or singlet state for its spin state. Light emitted from singlet exciton radiates fluorescence and light emitted from triplet exciton radiates phosphorescence. Phosphorescence achieves 3-fold efficiency comparing to fluorescence and may greatly enhance the IQE (internal quantum efficiency) of devices up to 100% by adopting metal complexes in electroluminescent configuration to achieve strong spin-orbital coupling and mixing of singlets and triplets. Therefore, phosphorescent metal complexes are now adopted as phosphorescent dopants in the emitting layer of OLED. In addition, the doping method of doping the emitting material into host emitting material is generally used to reduce the self-quenching of the emitting material. Therefore, the search for host emitting materials becomes noteworthy since host emitting materials must be capable of capturing carriers and have good energy transfer properties, high glass transition temperature, high thermal stability and appropriate energy gap of the singlet and triplet excited states. However, it would be difficult to obtain host emitting materials that fully meet the criteria and there is still some room for host emitting material development in OLED.

The hunt for efficient blue electroluminescence material is of particular interest because it is an essential component to realize OLEDs in display as well as lighting applications. Many research groups have successfully prepared efficient blue fluorophores and the OLED thereof. However, the efficient ones with good Commission Internationale d'Énclairage y coordinate value ($CIE_y$) ≤0.15 are still relatively rare. At the present time, there is a lack of good organic electroluminescence compounds that will satisfy the aforementioned need.

SUMMARY OF THE INVENTION

One objective of the present invention provides an asymmetric styrene derivative having carbazole and aniline, it provided with main BCzVBi structure but impair the symmetry of BCzVBi so as to increase the solubility of the dopant material and applicability in OLED solution process.

According to one embodiment of the present invention, an asymmetric styrene derivative having carbazole and aniline is represented by formula (I):

wherein R1 is selected from the group consisting of hydrogen, substituted or unsubstituted $C_1$-$C_{20}$ alkyl, substituted or unsubstituted aryl and substituted or unsubstituted heteroaryl, R2 and R3 are selected from substituted or unsubstituted $C_1$-$C_{20}$ alkyl, substituted or unsubstituted aryl and substituted or unsubstituted heteroaryl.

Another objective of the present invention provides an organic light emitting diode with high efficiency performance.

According to another embodiment of the present invention, an organic light emitting diode comprises a cathode, a anode and an emitting layer disposed between the cathode and the anode, wherein the emitting layer comprises the asymmetric styrene derivative aforementioned The asymmetric styrene derivative of the present invention may provide with blue emitting property to be a dopant emitting material.

The purpose, technical content, characteristic and effect of the present invention will be easy to understand by reference to the following detailed descriptions, when taken in conjunction with the accompanying drawings and the particular embodiment.

DESCRIPTION OF THE PREFERRED EMBODIMENT

In known materials, BCzVBi is a blue electroluminescence material with quite efficiency. One of the disadvantages of BCzVBi is poor solubility (<0.5% wt), such that BCzVBi is unable to apply in solution process so as limited the application. Therefore, it is now a current goal to develop a novel, efficient blue electroluminescence material.

BCzVBi

One objective of the present invention provides novel asymmetric styrene derivatives having carbazole and aniline, which are provided with main BCzVBi structure but impair the symmetry of BCzVBi so as to increase the solubility of the dopant material and applicability in OLED solution process.

According to the present invention, an asymmetric styrene derivative having carbazole and aniline is represented by formula (I):

wherein R1 is selected from the group consisting of hydrogen, substituted or unsubstituted $C_1$-$C_{20}$ alkyl, substituted or unsubstituted aryl and substituted or unsubstituted heteroaryl. R2 and R3 are independently selected from the group consisting of substituted or unsubstituted $C_1$-$C_{20}$ alkyl, substituted or unsubstituted aryl and substituted or unsubstituted heteroaryl. R2 and R3 may be identical or different.

According the present invention, an asymmetric styrene derivative having carbazole and aniline is represent represented by formula (II):

wherein R4 is selected from the group consisting of hydrogen, substituted or unsubstituted halogen, substituted or unsubstituted $C_1$-$C_{20}$ alkyl, substituted or unsubstituted aryl, and substituted or unsubstituted heteroaryl.

Here, "aryl" refers to a hydrocarbon moiety having one or more aromatic rings. For example, carbon number of aryl moieties may be 6 to 20. Examples of aryl moieties include phenyl (Ph), phenylene, naphthyl, naphthylene, pyrenyl, anthryl, and phenanthryl.

"Heteroaryl" refers to a hydrocarbon moiety having one or more aromatic rings, and the aromatic rings comprise at least one heteroatom (e.g., N, O, or S). For example, carbon number of heteroaryl moieties may be 2 to 20. Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties. Possible substituents on cycloalkyl, cycloalkenyl, heterocycloalkyl, heterocycloalkenyl, aryl, and heteroaryl comprise, but are not limited to, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halogen, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Preferably, R1 is selected from the group consisting of $C_1$-$C_{20}$ alkyl, heteroaryl, aryl, $C_1$-$C_{20}$ alkyl substituted aryl, $C_1$-$C_{20}$ haloalkyl substituted aryl, amino substituted aryl, halogen substituted aryl, heteroaryl substituted aryl, aryl substituted heteroaryl, $C_1$-$C_{20}$ alkyl substituted heteroaryl, $C_1$-$C_{20}$ haloalkyl substituted heteroaryl, halogen substituted heteroaryl and heteroaryl substituted heteroaryl.

Preferably, R2 and R3 are selected from the group consisting of $C_1$-$C_{20}$ alkyl, heteroaryl, aryl, aryl substituted aryl, $C_1$-$C_{20}$ alkyl substituted aryl, $C_1$-$C_{20}$ haloalkyl substituted aryl, amino substituted aryl, halogen substituted aryl, and heteroaryl substituted aryl.

Preferably, R4 is selected from the group consisting of $C_1$-$C_{20}$ alkyl, heteroaryl, aryl, aryl substituted aryl, $C_1$-$C_{20}$ alkyl substituted aryl, $C_1$-$C_{20}$ haloalkyl substituted aryl, amino substituted aryl, halogen substituted aryl, heteroaryl substituted aryl, aryl substituted heteroaryl, $C_1$-$C_{20}$ alkyl substituted heteroaryl, $C_1$-$C_{20}$ haloalkyl substituted heteroaryl, halogen substituted heteroaryl and heteroaryl substituted heteroaryl.

The compound of the embodiment in the present invention is disclosed below.

Synthetic Method

Example: PCzDPA

Take PCzDPA (N,N-diphenyl-4-[(E)-2-(4-{4-[(E)-2-(9-phenyl-9H-carbazol-3-yl)ethenyl]phenyl}phenyl)ethenyl]aniline) for example, the synthetic method thereof is as follows.

-continued

+

PCzDPA

PCzDPA

The remaining compounds are synthesized by the following method.

+

The spectral data of the compound are provided as follows:

PCzDPA (N,N-diphenyl-4-[(E)-2-(4-{4-[(E)-2-(9-phenyl-9H-carbazol-3-yl)ethenyl]phenyl}phenyl)ethenyl]aniline)

$^1$H NMR (400 MHz, CDCl3) δ 8.28 (s, 1H), 8.17 (d, J=7.6 Hz, 1H), 7.65-7.55 (m, 11H), 7.47 (dd, J=8.4 Hz, J=7.2 Hz, 2H), 7.40-7.38 (m, 4H), 7.35 (d, J=11.2 Hz, 2H), 7.32-7.23 (m, 6H), 7.19 (d, J=16.4 Hz, 2H), 7.12-7.00 (m, 9H).

PCzNA (N-phenyl-N-{4-[(E)-2-(4-{4-[(E)-2-(9-phenyl-9H-carbazol-3-yl)ethenyl]phenyl}phenyl)ethenyl]phenyl}naphthalen-1-amine)

$^1$H NMR (400 MHz, CDCl3) δ 8.28 (s, 1H), 8.17 (d, J=7.6 Hz, 1H), 7.90 (dd, J=8.4 Hz, 2H), 7.77 (d, J=8.0 Hz, 1H), 7.59-7.28 (m, 24H), 7.22-7.18 (m, 4H), 7.08-6.94 (m, 7H).

PCzDFA

N,N-bis(4-fluorophenyl)-4-[(E)-2-(4-{4-[(E)-2-(9-phenyl-9H-carbazol-3-yl)ethenyl]phenyl}phenyl) ethenyl]aniline $^1$H NMR (400 MHz, CDCl3) δ 8.28 (s, 1H), 8.17 (d, J=6.8 Hz, 1H), 7.63-7.55 (m, 9H), 7.47 (dd, J=6.8 Hz, J=7.2 Hz, 2H), 7.40-7.38 (m, 4H), 7.35 (d, J=11.6 Hz, 2H), 7.32-7.23 (m, 6H), 7.19 (d, J=16.4 Hz, 2H), 7.12-7.00 (m, 9H).

PCzDMA

N,N-bis(4-methylphenyl)-4-[(E)-2-(4-{4-[(E)-2-(9-phenyl-9H-carbazol-3-yl)ethenyl]phenyl}phenyl) ethenyl]aniline $^1$H NMR (400 MHz, CDCl3): δ 8.28 (s, 1H), 8.17 (d, J=7.6 HZ, 1H), 7.63-7.54 (m, 11H), 7.47 (dd, J=6.8 Hz, J=7.2 Hz, 2H), 7.41-7.28 (m, 8H), 7.18 (d, J=16 Hz, 2H), 7.11-6.97 (m, 11H).

Refers to Table. 1, which shows the absorption and emission spectra of the compound of the present invention, wherein the compound of the present invention is used as blue emitting material.

Figure 1:
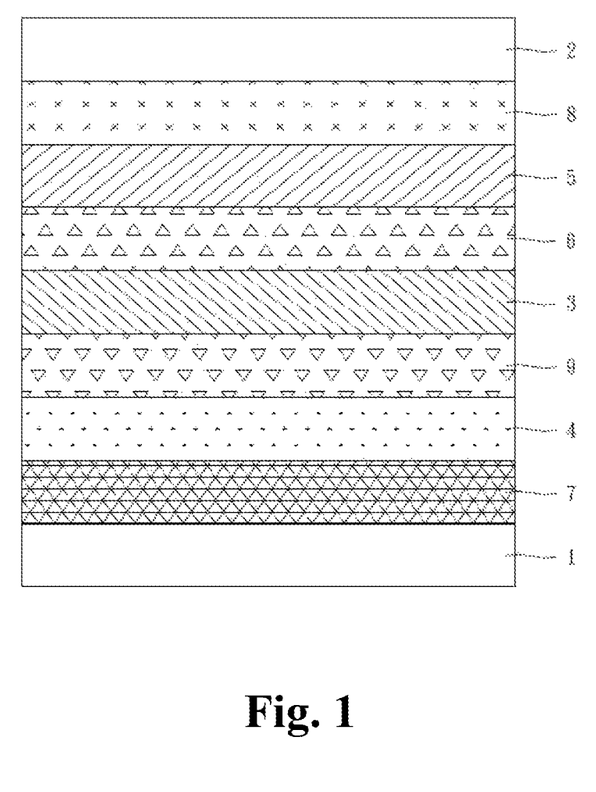
FIG. 1 is a schematic diagram illustrating structure of a light-emitting device with asymmetric styrene derivative.

In addition, referring to FIG. 1, FIG. 1 is a schematic diagram illustrating an embodiment of organic light emitting diode including the compound. The organic light emitting diode comprises the structure of emitting layer 3, which is disposed between cathode 1 and anode 2 and comprises the compound. Emitting layer 3 is formed by doping emitting materials into host emitting material. The structure of emitting element further comprises a hole injecting layer 7, a hole transport layer 4, an electron blocking layer 9, an emitting layer 3, a hole blocking layer 6, an electron transport layer 5 and an electron injecting layer 8 sequentially configured on top of the anode 1. The real thickness of each layer doesn't correspond to the schematic size. The hole injecting layer 7, electron blocking layer 9, hole blocking layer 6 and electron injecting layer 8 may be optional. The compound of the present invention may be a dopant emitting material of the emitting layer.

Figure 2:
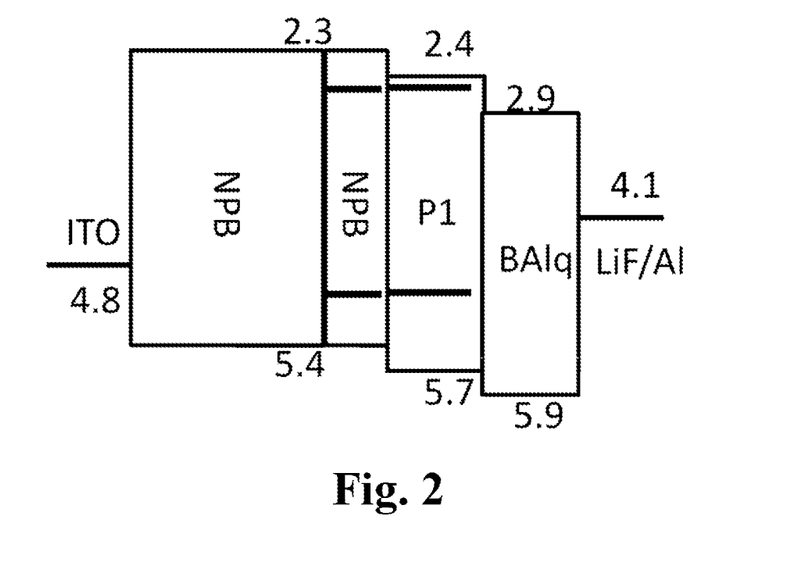
FIG. 2 is a schematic diagram illustrating structure of a light-emitting device with asymmetric styrene derivative of the embodiment in present invention.

Referring to FIG. 2, according to the embodiment of the present invention, in the resulting device structure, the subsrate is made of ITO, tested electrode materials include LiF/Al; tested emitting materials include P1 (DMPPP, as the following formula); tested electron transporting layer includes BCP (2,9-dimethyl-4,7-diphenyl-[1,10]phenanthroline) and Alq3 (tris(8-hydroxyquinoline)aluminum(III)), which may be used for the hole blocking layer or be used for the hole blocking layer and electron transporting layer, simultaneously. Tested hole transporting layer includes NPB (4,4'-bis[N-(1-naphthyl)-N-phenyl-amino]bipheny), which may be used for electron blocking layer or for electron blocking layer and hole transporting layer, simultaneously.

DMPPP

TABLE 1

The absorption and emission spectra and physical property of the present invention

| compound | $\lambda_{abs}$[a] [nm] | $\lambda_{fl}$[a] [nm] | $\lambda_{fl}$[b] [nm] | $E_g$[c] [eV] | HOMO[d] [eV] | LUMO[e] [eV] | $T_g/T_m/T_d$ (° C.) | Q.Y.[f] |
|---|---|---|---|---|---|---|---|---|
| PCzDFA | 385 | 444 | 486 | 2.78 | 5.55 | 2.77 | 107/253/460 | >0.90 |
| PCzNA | 388 | 446 | 492 | 2.82 | 5.38 | 2.56 | 110/256/470 | >0.90 |
| PCzDPA | 387 | 446 | 490 | 2.81 | 5.32 | 2.51 | —/—/— | >0.90 |
| PCzDMA | 394 | 454 | 491 | 2.75 | 5.28 | 2.53 | —/222/451 | >0.90 |

Note:
[a]Absorption and fluorescence spectra are measured in toluene solution with concentration of 1 × 10$^{-5}$M.
[b]Fluorescence spectra is measured in film (25 nm).
[c]Estimated by film optical emission threshold.
[d]Estimated by optical spectroscopy (AV-II).
[e]LUMO = HOMO − $E_g$
[f]Quantum yield is measured in cyclohexane, and take 9,10-diphenylanthrecene (Q.Y. = 0.90) as standard value.

The element devices of the presnet invention are as follows:
A: NPB(60 nm)/NPB:3% PCzDFA (10 nm)/P1:3% PCzDFA (15 nm)/BAlq(20 nm)/LiF(1 nm)/Al(100 nm)
B: NPB(60 nm)/NPB:3% PCzNA(10 nm)/P1:3% PCzNA (15 nm)/BAlq(20 nm)/LiF(1 nm)/Al(100 nm)
C: NPB(60 nm)/NPB:3% PCzDPA (10 nm)/P1:3% PCzDPA (15 nm)/BAlq(20 nm)/LiF(1 nm)/Al(100 nm
D: NPB(60 nm)/NPB:3% PCzDMA (10 nm)/P1:3% PCzDMA (15 nm)/BAlq(20 nm)/LiF(1 nm)/Al(100 nm)
E: NPB(60 nm)/NPB:5% BCzVBi (10 nm)/P1:5% BCzVBi (15 nm)/BAlq(20 nm)/LiF(1 nm)/Al(100 nm)

TABLE 2

The element performance of devices using the compounds of the present invention as dopant

| device | dopant | $V_d$ [V] | $L_{max}$ (Cd/m², V) | $\eta_{ext, max}$ [%, V] | $\eta_{c, max}$ [cd/A, V] | $\eta_{p, max}$ [lm/W, V] | $\lambda_{max}$ at 8 V [nm] | CIE, (x, y) at 8 V |
|---|---|---|---|---|---|---|---|---|
| A | PCzDFA | 2.76 | 49760, 18.5 | 8.4, 6.5 | 9.2, 6.5 | 5.3, 5.0 | 454 | (0.14, 0.12) |
| B | PCzNA | 2.77 | 57943, 18.5 | 9.4, 8.0 | 10.3, 8.0 | 4.9, 6.0 | 456 | (0.14, 0.12) |
| C | PCzDPA | 2.86 | 64857, 18.5 | 9.7, 8.0 | 12.4, 8.0 | 6.1, 5.5 | 458 | (0.14, 0.15) |
| D | PCzDMA | 2.58 | 66261, 19.0 | 7.7, 5.0 | 10.5, 5.0 | 7.4, 4.0 | 462 | (0.13, 0.17) |
| E | BCzVBi | 2.76 | 52455, 18.0 | 9.2, 5.5 | 9.4, 5.5 | 5.7, 5.0 | 448 | (0.14, 0.11) |

Referring to Table. 2, the maximum external performance values of the devices A, B and C all exceed 8.0, and reach to 8.4, 9.4, 9.7, respectively. The maximum emitting values of the devices B, C and D are all greater than that of the control group E with BczVBi.

TABLE 3

The element performance of devices using compounds of the present invention as dopant

| device | dopant | $\eta_{ext}$ [%, V] (1000 cd m⁻²) | $\eta_c$ [cd/A, V] (1000 cd m⁻²) | $\eta_p$ [lm/W, V] (1000 cd m⁻²) | $\eta_{ext}$ [%, V] (3000 cd m⁻²) | $\eta_c$ [cd/A, V] (3000 cd m⁻²) | $\eta_p$ [lm/W, V] (3000 cd m⁻²) |
|---|---|---|---|---|---|---|---|
| A | PCzDFA | 8.4, 6.0 | 9.2, 6.0 | 4.8, 6.0 | 8.4, 7.0 | 9.1, 7.0 | 4.1, 7.0 |
| B | PCzNA | 9.3, 7.0 | 10.2, 7.0 | 4.6, 7.0 | 9.4, 8.0 | 10.3, 8.0 | 4.0, 8.0 |
| C | PCzDPA | 9.6, 7.0 | 12.4, 7.0 | 5.5, 7.0 | 9.7, 8.0 | 12.4, 8.0 | 4.9, 8.0 |
| D | PCzDMA | 7.6, 5.5 | 10.5, 5.5 | 6.0, 5.5 | 7.5, 6.5 | 10.4, 7.0 | 5.0, 6.5 |

Referring to Table. 4, the solubility of the examplary compound of the present invention is evaluated in comparison to BczVBi, the soubility of PCzDFA•PCzDMA in toluene may be greater than 2 wt %.

TABLE 4

The solubility of the compound of the present invention in toluene.

| compound | Solubility |
|---|---|
| PCzDFA | >2 wt % |
| PCzNA | >1 wt % |
| PCzDPA | >1 wt % |
| PCzDMA | >2 wt % |

In one embodiment, the examplary compounds of the present invention may be used for solution process, the decices are as follows:
A: PEDOT:PSS (300 rpm 5 sec, 2500 rpm 25 sec)/PO—C₆: 3% PCzDPA (2000 rpm 30 sec)/TPBI (40)
B: PEDOT:PSS (300 rpm 5 sec, 2500 rpm 25 sec)/PO—C₆: 3% PCzDPA (2500 rpm 30 sec)/TPBI (40)

PO-C6

TABLE 5

The performance of devices using the compounds of the
present invention as dopant and using the solution process

| device | dopant | $V_d$ [V] | $L_{max}$ ($Cd/m^2$, V) | $\eta_{ext, max}$ [%,V] | $\eta_{c, max}$ [cd/A, V] | $\eta_{p, max}$ [lm/W, V] | $\lambda_{max}$ at 8 V [nm] | CIE, (x, y) at 8 V |
|---|---|---|---|---|---|---|---|---|
| A | PCzDPA | 3.28 | 15323, 15.5 | 4.4, 8.0 | 7.4, 8.0 | 4.3, 4.0 | 462 | (0.14, 0.22) |
| B | PCzDPA | 3.24 | 18080, 15.0 | 4.5, 7.5 | 7.8, 7.5 | 5.0, 4.0 | 462 | (0.14, 0.23) |

As decribe above, the present invention provides asymmetric styrene derivatives having carbazole and aniline, which are provided with main BCzVBi structure but impair the symmetry of BCzVBi so as to increase the solubility and applicability in OLED solution process.

The foregoing embodiments are used only for illustrating the technical ideas and characteristics of the present invention, it is purposed to make person ordinary skill in the art to understand and implement the present invention, but for limitation to the claims of the present invention. That is, the equivalent change and modification according to the sprit disclosed in the present invention should be covered by the appended claims.

What is claimed is:

1. An asymmetric styrene derivative having carbazole and aniline, represented by formula (I):

(1)

wherein R1 is selected from the group consisting of hydrogen, substituted or unsubstituted $C_1$-$C_{20}$ alkyl, substituted or unsubstituted aryl and substituted or unsubstituted heteroaryl, R2 and R3 are selected from substituted or unsubstituted $C_1$-$C_{20}$ alkyl, substituted or unsubstituted aryl and substituted or unsubstituted heteroaryl.

2. The asymmetric styrene derivative having carbazole and aniline as claimed in claim 1, wherein R2 and R3 are selected from the group consisting of $C_1$-$C_{20}$ alkyl, heteroaryl, aryl, aryl substituted aryl, $C_1$-$C_{20}$ alkyl substituted aryl, $C_1$-$C_{20}$ haloalkyl substituted aryl, amino substituted aryl, halogen substituted aryl, heteroaryl substituted aryl.

3. The asymmetric styrene derivatives having carbazole and aniline as claimed in claim 1, wherein R1 is selected from the group consisting of $C_1$-$C_{20}$ alkyl, heteroaryl, aryl, aryl substituted aryl, $C_1$-$C_{20}$ alkyl substituted aryl, $C_1$-$C_{20}$ haloalkyl substituted aryl, amino substituted aryl, halogen substituted aryl, heteroaryl substituted aryl, aryl substituted heteroaryl, $C_1$-$C_{20}$ alkyl substituted heteroaryl, $C_1$-$C_{20}$ haloalkyl substituted heteroaryl, halogen substituted heteroaryl and heteroaryl substituted heteroaryl.

4. The asymmetric styrene derivatives having carbazole and aniline as claimed in claim 1, represented by formula (II):

wherein R4 is selected from the group consisting of hydrogen, substituted or unsubstituted halogen, substituted or unsubstituted $C_1$-$C_{20}$ alkyl, substituted or unsubstituted aryl and substituted or unsubstituted heteroaryl.

5. The asymmetric styrene derivative having carbazole and aniline as claimed in claim 4, wherein R4 is selected from the group consisting of $C_1$-$C_{20}$ alkyl, heteroaryl, aryl, aryl substituted aryl, $C_1$-$C_{20}$ alkyl substituted aryl, $C_1$-$C_{20}$ haloalkyl substituted aryl, amino substituted aryl, halogen substituted aryl, heteroaryl substituted aryl, aryl substituted heteroaryl, $C_1$-$C_{20}$ alkyl substituted heteroaryl, $C_1$-$C_{20}$ haloalkyl substituted heteroaryl, halogen substituted heteroaryl and heteroaryl substituted heteroaryl.

6. An organic light emitting diode, comprising:
   a cathode;
   an anode; and
   an emitting layer, disposed between the cathode and the anode, wherein the emitting layer comprises a asymmetric styrene derivative having carbazole and aniline represented by formula (I):

wherein R1 is selected from the group consisting of hydrogen, substituted or unsubstituted $C_1$-$C_{20}$ alkyl, substituted or unsubstituted aryl and substituted or unsubstituted heteroaryl, R2 and R3 are selected from the group consisting of substituted or unsubstituted $C_1$-$C_{20}$ alkyl, substituted or unsubstituted aryl and substituted or unsubstituted heteroaryl.

7. The organic light emitting diode as claimed in claim 6, wherein R2 and R3 are selected from the group consisting of $C_1$-$C_{20}$ alkyl, heteroaryl, aryl, aryl substituted aryl, $C_1$-$C_{20}$ alkyl substituted aryl, $C_1$-$C_{20}$ haloalkyl substituted aryl, amino substituted aryl, halogen substituted aryl and heteroaryl substituted aryl.

8. The organic light emitting diode as claimed in claim 6, wherein R1 is selected from the group consisting of $C_1$-$C_{20}$ alkyl, heteroaryl, aryl, aryl substituted aryl, $C_1$-$C_{20}$ alkyl substituted aryl, $C_1$-$C_{20}$ haloalkyl substituted aryl, amino substituted aryl, halogen substituted aryl, heteroaryl substituted aryl, aryl substituted heteroaryl, $C_1$-$C_{20}$ alkyl substituted heteroaryl, $C_1$-$C_{20}$ haloalkyl substituted heteroaryl, halogen substituted heteroaryl and heteroaryl substituted heteroaryl.

9. The organic light emitting diode as claimed in claim 6 wherein the asymmetric styrene derivative having carbazole and aniline is represented by formula (II):

wherein R4 is selected from the group consisting of hydrogen, substituted or unsubstituted halogen, substituted or unsubstituted $C_1$-$C_{20}$ alkyl, substituted or unsubstituted aryl and substituted or unsubstituted heteroaryl.

10. The organic light emitting diode as claimed in claim 9, wherein R4 is selected from the group consisting of $C_1$-$C_{20}$ alkyl, heteroaryl, aryl, aryl substituted aryl, $C_1$-$C_{20}$ alkyl substituted aryl, $C_1$-$C_{20}$ haloalkyl substituted aryl, amino substituted aryl, halogen substituted aryl, heteroaryl substituted aryl, aryl substituted heteroaryl, $C_1$-$C_{20}$ alkyl substituted heteroaryl, $C_1$-$C_{20}$ haloalkyl substituted heteroaryl, halogen substituted heteroaryl and heteroaryl substituted heteroaryl.

11. The organic light emitting diode as claimed in claim 6, wherein the organic emitting diode is a blue emitting diode.

12. The organic light emitting diode as claimed in claim 6, wherein the asymmetric styrene derivative having carbazole and aniline is a dopant emitting material.

\* \* \* \* \*